(12) United States Patent
Huang et al.

(10) Patent No.: US 12,324,659 B2
(45) Date of Patent: Jun. 10, 2025

(54) INFORMATION PROCESSING DEVICE, WALKING ENVIRONMENT DETERMINATION DEVICE, WALKING ENVIRONMENT DETERMINATION SYSTEM, INFORMATION PROCESSING METHOD, AND STORAGE MEDIUM

(71) Applicant: NEC Corporation, Tokyo (JP)

(72) Inventors: Chenhui Huang, Tokyo (JP); Kenichiro Fukushi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 722 days.

(21) Appl. No.: 17/612,620

(22) PCT Filed: May 29, 2019

(86) PCT No.: PCT/JP2019/021424
§ 371 (c)(1),
(2) Date: Nov. 19, 2021

(87) PCT Pub. No.: WO2020/240753
PCT Pub. Date: Dec. 3, 2020

(65) Prior Publication Data
US 2022/0240812 A1    Aug. 4, 2022

(51) Int. Cl.
*A61B 5/103* (2006.01)
*A61B 5/00* (2006.01)
*A61B 5/11* (2006.01)

(52) U.S. Cl.
CPC ............ *A61B 5/1038* (2013.01); *A61B 5/112* (2013.01); *A61B 5/6807* (2013.01); *A61B 5/7267* (2013.01)

(58) Field of Classification Search
CPC ..... A61B 5/1038; A61B 5/112; A61B 5/6807; A61B 5/7267; G01D 21/00; G01L 5/00
See application file for complete search history.

(56) References Cited

U.S. PATENT DOCUMENTS

| | | | |
|---|---|---|---|
| 2004/0249316 A1 | 12/2004 | Ashihara et al. | |
| 2010/0271051 A1 | 10/2010 | Sankai et al. | |
| 2011/0054359 A1* | 3/2011 | Sazonov | A61B 5/1118 |
| | | | 600/595 |
| 2017/0238845 A1 | 8/2017 | Wei et al. | |

(Continued)

FOREIGN PATENT DOCUMENTS

| | | |
|---|---|---|
| JP | 3833921 B2 | 10/2006 |
| JP | WO2009/084387 A1 | 5/2011 |

(Continued)

OTHER PUBLICATIONS

International Search Report for PCT Application No. PCT/JP2019/021424, mailed on Jul. 30, 2019.
Naomasa Horie, Takashi Mitsuda, Sadao Kawamura. "An Algorithm for Estimating Walking Types Using Foot-pressure Sensors". Transactions of Japanese Society for Medical and Biological Engineering. 2006, vol. 44, No. 4, pp. 621-627.
Koki Hayama, Hiroya Fukuda, "Estimation of Center of Pressure Trajectory Using an Insole-Type Force Sensor". Transactions of Japanese Society for Medical and Biological Engineering. Feb. 10, 2016, vol. 54, No. 1, pp. 15-21.

(Continued)

*Primary Examiner* — Michael R Bloch
*Assistant Examiner* — Abid A Mustansir
(74) *Attorney, Agent, or Firm* — Sughrue Mion, PLLC

(57) ABSTRACT

Provided is an information processing device including an acquisition unit configured to acquire load information based on a load applied to a load measurement device from a sole of a user and a feature amount extracting unit configured to extract a feature amount indicating a walking environment from time series data in at least one walking cycle included in the load information.

15 Claims, 20 Drawing Sheets

(56) References Cited

U.S. PATENT DOCUMENTS

2019/0101387 A1    4/2019   Jackson et al.
2020/0178849 A1*   6/2020   Cheng .................... A61B 5/112

FOREIGN PATENT DOCUMENTS

| | | |
|---|---|---|
| JP | 4877909 B2 | 2/2012 |
| JP | 2013-070787 A | 4/2013 |
| JP | 2013-072729 A | 4/2013 |
| JP | 5590301 B2 | 9/2014 |
| JP | 2015-055510 A | 3/2015 |
| JP | 6054905 B2 | 12/2016 |
| JP | 2017-144237 A | 8/2017 |

OTHER PUBLICATIONS

Yusuke Ohashi, Yu Enokibori, Kenji Mase, "Identification of the road surface context using the maximum pressure selection when walking". IPSJ SIG Technical Report. Oct. 7, 2014, vol. 2014-UBI-44, No. 17, pp. 1-8.

Ayumi Onishi, Tsutomu Terada, Masahiko Tsukamoto, "Posture Recognition Method Using Foot Pressure Distribution". IPSJ Symposium Series: Multimedia, Distributed, Cooperative and Mobile Symposium (DICOM02017). Jun. 28, 2017, vol. 2017, No. 1, pp. 810-818.

* cited by examiner

FIG. 11

| | EXPLANATORY VARIABLE | | | | RESPONSE VARIABLE |
|---|---|---|---|---|---|
| TIME OF THE PEAK OF FIRST TIME SERIES DATA | SIZE OF THE PEAK OF FIRST TIME SERIES DATA | TIME OF THE PEAK OF SECOND TIME SERIES DATA | SIZE OF THE PEAK OF SECOND TIME SERIES DATA | ... | WALKING STATE LABEL |
| A1 | B1 | C1 | D1 | ... | LEVEL GROUND |
| A2 | B2 | C2 | D2 | ... | ASCENDING STAIRS |
| ... | ... | ... | ... | ... | ... |

FIG. 16

| | EXPLANATORY VARIABLE | | | | | RESPONSE VARIABLE |
|---|---|---|---|---|---|---|
| TIME OF P1 | SIZE OF P1 | TIME OF P2 | SIZE OF P2 | TIME DIFFERENCE BETWEEN P1 AND P2 | ... | WALKING STATE LABEL |
| A1 | B1 | C1 | D1 | E1 | ... | LEVEL GROUND |
| A2 | B2 | C2 | D2 | E2 | ... | ASCENDING STAIRS |
| ... | ... | ... | ... | ... | ... | ... |

INFORMATION PROCESSING DEVICE, WALKING ENVIRONMENT DETERMINATION DEVICE, WALKING ENVIRONMENT DETERMINATION SYSTEM, INFORMATION PROCESSING METHOD, AND STORAGE MEDIUM

This application is a National Stage Entry of PCT/JP2019/021424 filed on May 29, 2019, the contents of all of which are incorporated herein by reference, in their entirety.

TECHNICAL FIELD

The present invention relates to an information processing device, a walking environment determination device, a walking environment determination system, an information processing method, and a storage medium.

BACKGROUND ART

Patent Literature 1 discloses a system for measuring a walking state using three-dimensional angle information of a knee, pressure information or the like.

CITATION LIST

Patent Literature

PTL 1: Japanese Patent Application Laid-open No. 2017-144237

SUMMARY OF INVENTION

Technical Problem

In connection with the measurement of the walking state, a determination of a walking environment such as whether or not a location where the user is walking is level ground may be further required. In the method for measuring a walking state as disclosed in Patent Literature 1, depending on elements used for determining a walking state, a walking environment may not be accurately determined.

The present invention intends to provide an information processing device, a walking environment determination device, a walking environment determination system, an information processing method, and a storage medium which can suitably extract a feature amount used for determining a walking environment.

Solution to Problem

According to one example aspect of the invention, provided is an information processing device including an acquisition unit configured to acquire load information based on a load applied to a load measurement device from a sole of a user and a feature amount extracting unit configured to extract a feature amount indicating a walking environment from time series data in at least one walking cycle included in the load information.

According to another example aspect of the invention, provided is an information processing method including acquiring load information based on a load applied to a load measurement device from a sole of a user and extracting a feature amount indicating a walking environment from time series data in at least one walking cycle included in the load information.

According to another example aspect of the invention, provided is a storage medium storing a program that causes a computer to perform acquiring load information based on a load applied to a load measurement device from a sole of a user and extracting a feature amount indicating a walking environment from time series data in at least one walking cycle included in the load information.

Advantageous Effects of Invention

According to the present invention, an information processing device, a walking environment determination device, a walking environment determination system, an information processing method, and a storage medium which can suitably extract a feature amount used for determining a walking environment can be provided.

BRIEF DESCRIPTION OF DRAWINGS

FIG. 11 is a table schematically illustrating a correspondence relation between a feature amount vector and a walking state label acquired by a training process.

FIG. 16 is a table schematically illustrating a correspondence relation between a feature amount vector and a walking state label acquired by a training process.

DESCRIPTION OF EMBODIMENTS

Exemplary embodiments of the present invention are described below with reference to the drawings. Throughout the drawings, the same components or corresponding components are labeled with same references, and the description thereof may be omitted or simplified.

First Example Embodiment

A walking environment determination system according to the present example embodiment is described. The walking environment determination system of the present example embodiment is a system for measuring and analyzing a walking state including determination of a walking environment of a user. In this specification, the "walking environment" means a state of the ground where the user is walking. More specifically, the "walking environment" refers to, for example, a location where the user is walking is level ground or a location other than level ground such as stairs or a slope. The "walking state" includes, in addition to the walking environment, a feature included in the walking pattern of the user (gait).

Figure 1:
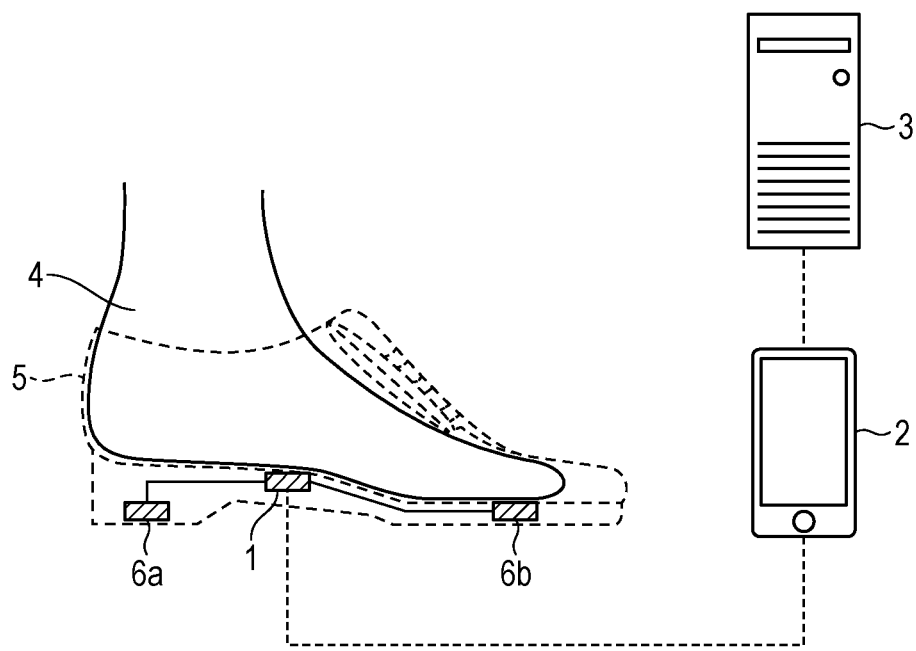
FIG. 1 is a schematic diagram illustrating a general configuration of a walking environment determination system according to a first example embodiment.

FIG. 1 is a schematic diagram illustrating a general configuration of a walking environment determination system according to the present example embodiment. The walking environment determination system includes a walking environment determination device 1, an information communication terminal 2, a server 3, and load measurement devices 6a and 6b, which can be connected to each other by wireless communication. The load measurement device 6a may be referred to as a first load measurement device, and the load measurement device 6b may be referred to as a second load measurement device.

The walking environment determination device 1 and the load measurement devices 6a and 6b are provided to be close to the sole of a shoe 5 worn by a user 4, for example. The walking environment determination device 1 and the load measurement device 6a, and the walking environment determination device 1 and the load measurement device 6b are communicatively connected by wiring or the like. The load measurement devices 6a and 6b are sensors for measuring load received from the sole of the user 4. The load measurement devices 6a and 6b convert load received from the user 4 into electrical signals and output the electrical signals to the walking environment determination device 1 under the control of the walking environment determination device 1. The load conversion method of the load measurement devices 6a and 6b may be a spring type, a piezoelectric element type, a magnetostrictive type, an electrostatic capacitance type, a gyro type, a strain gauge type, or the like, but is not particularly limited. The load measurement devices 6a and 6b are sometimes referred to as load cells. The walking environment determination device 1 is an electronic apparatus having a control function of the load measurement devices 6a and 6b, an information processing function of analyzing measured load information, a communication function with the information communication terminal 2, or the like.

Note that, the walking environment determination device 1 and load measurement devices 6a and 6b may be provided in the insole of the shoe 5, may be provided in the outsole of the shoe 5, or may be embedded in the shoe 5. The walking environment determination device 1 and the load measurement devices 6a and 6b may be detachably attached to the shoe 5 or may be non-detachably fixed to the shoe 5. The walking environment determination device 1 and the load measurement devices 6a and 6b may be provided at a portion other than the shoe 5 as long as the walking environment determination device 1 can measure the load of the foot. For example, the walking environment determination device 1 may be provided in a sock which the user 4 is wearing, provided in a decoration, directly attached to the foot of the user 4, or embedded in the foot of the user 4. Although FIG. 1 illustrates an example in which one walking environment determination device 1 and two load measurement devices 6a and 6b are provided on one foot of the user 4, one walking environment determination device 1 and two load measurement devices 6a and 6b may be provided on each of both feet of the user 4. In this case, the load information of both feet can be acquired in parallel, and more information can be acquired.

In this specification, the "foot" means a body part below an ankle of the user 4. In addition, in this specification, the "user" means a person who is an object of determination of a walking environment using the walking environment determination device 1. Whether or not the user corresponds to the "user" is unrelated to whether or not the user is a user of a device other than the walking environment determination device 1 constituting the walking environment determination system, whether or not the user receives a service provided by the walking environment determination system, or the like.

The information communication terminal 2 is a terminal device carried by the user 4, such as a cellular phone, a smartphone, or a smart watch. Application software for analyzing a walking state is installed in advance in the information communication terminal 2, and a process based on the application software is performed. The information communication terminal 2 acquires data such as the determination result of the walking environment and the walking state acquired by the walking environment determination device 1 from the walking environment determination device 1 and performs information processing using the data. The result of the information processing may be notified to the user 4 or may be transmitted to the server 3. The information communication terminal 2 may have a function of providing software such as a control program of the walking environment determination device 1 or a data analysis program to the walking environment determination device 1.

The server 3 provides application software for analyzing walking states to the information communication terminal 2 and updates the application software. The server 3 may store data acquired from the information communication terminal 2 and perform information processing using the data.

Note that, the general configuration is an example, and for example, the walking environment determination device 1 may be directly connected to the server 3. Further, the walking environment determination device 1 and the information communication terminal 2 may be configured as an integrated device, and another device such as an edge server or a relay device may be further included in the walking environment determination system.

Figure 2:
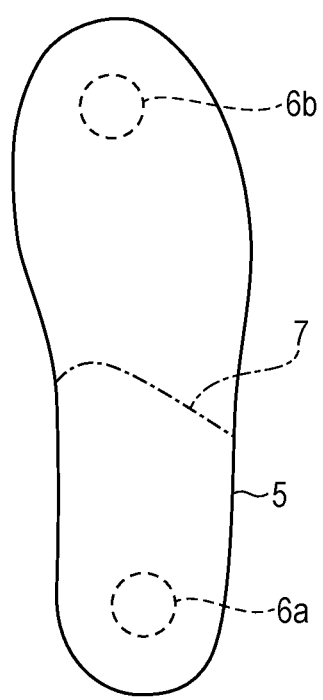
FIG. 2 is a schematic diagram illustrating an arrangement of a load measurement device according to the first example embodiment.

FIG. 2 is a schematic diagram illustrating an arrangement of load measurement devices 6a and 6b according to the present example embodiment. FIG. 2 is a perspective view of the shoe 5 viewed from the bottom side. The load measurement device 6a is provided at a position corresponding to the heel of the user 4, and the load measurement device 6b is provided between the toe and the load measurement device 6a. More specifically, the load measurement device 6a is provided between the position corresponding to the Lisfranc joint 7 of the foot (the joint between the metatarsal bone and the tarsal bone of the foot) and the heel, and the load measurement device 6b is provided between the position corresponding to the Lisfranc joint 7 of the foot and the toe. A dashed dotted line with reference numeral "7" in the figure indicates the position of the Lisfranc joint 7 when the user 4 wears the shoe 5.

Figure 3:
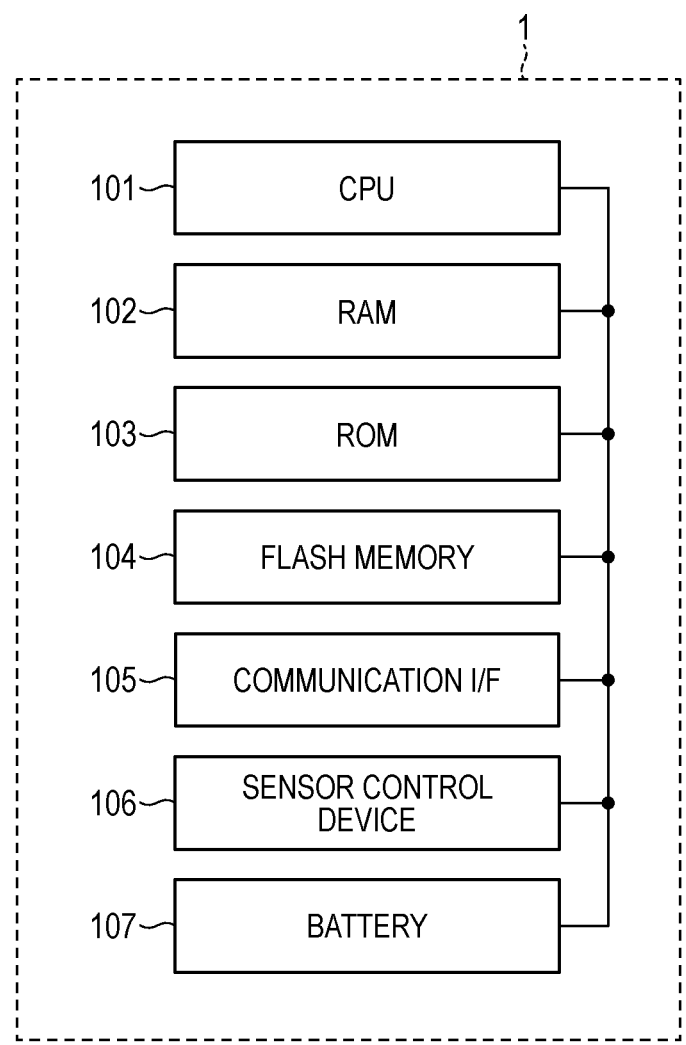
FIG. 3 is a block diagram illustrating a hardware configuration of a walking environment determination device according to the first example embodiment.

FIG. 3 is a block diagram illustrating a hardware configuration example of the walking environment determination device 1. The walking environment determination device 1 is, for example, a microcomputer or a microcontroller. The walking environment determination device 1 includes a central processing unit (CPU) 101, a random access memory (RAM) 102, a read only memory (ROM) 103, a flash memory 104, a communication interface (I/F) 105, a sensor control device 106, and a battery 107. Each unit in the walking environment determination device 1 is connected each other via a bus, wiring, a driving device, or the like.

The CPU 101 is a processor that performs predetermined calculation in accordance with a program stored in the ROM 103, the flash memory 104, or the like, and also has a function of controlling each unit of the walking environment determination device 1. The RAM 102 is composed of a volatile storage medium and provides a temporary memory area required for the operation of the CPU 101. The ROM 103 is composed of a non-volatile storage medium and stores necessary information such as a program used for the operation of the walking environment determination device 1. The flash memory 104 is a storage device composed of a non-volatile storage medium and temporarily storing data, storing an operation program of the walking environment determination device 1, or the like.

The communication I/F 105 is a communication interface based on standards such as Bluetooth (registered trademark) and Wi-Fi (registered trademark), and is a module for performing communication with the information communication terminal 2.

The sensor control device 106 is a control device that controls the load measurement devices 6a and 6b to measure load and acquires an electric signal indicating the load from the load measurement devices 6a and 6b. The acquired electrical signal is stored in the flash memory 104 as digital data. Thus, the walking environment determination device 1 can acquire the load measured by the load measurement devices 6a and 6b as time series data. The load measured by the load measurement device 6a may be referred to as first load information, and the load measured by the load measurement device 6b may be referred to as second load information. The time series data of the load measured by the load measurement device 6a may be referred to as first time series data, and the time series data of the load measured by the load measurement device 6b may be referred to as second time series data. Note that analog-to-digital (AD) conversion for converting analog signals measured by the load measurement devices 6a and 6b into digital data may be performed in the load measurement devices 6a and 6b, or may be performed by the sensor control device 106.

The battery 107 is, for example, a secondary battery, and supplies power necessary for the operations of the walking environment determination device 1. When power is required to be supplied to the load measurement devices 6a and 6b, the battery 107 may also supply power to the load measurement devices 6a and 6b. Since the battery 107 is built in the walking environment determination device 1, the walking environment determination device 1 can operate wirelessly without connecting to an external power source by wire.

Note that the hardware configuration illustrated in FIG. 3 is an example, and other devices may be added or some devices may not be provided. Further, some devices may be replaced by other devices having similar functions. For example, the walking environment determination device 1 may further include an input device such as a button so that an operation by the user 4 can be accepted, and may further include an output device such as a display, a display lamp, and a speaker for providing information to the user 4. Thus, the hardware configuration illustrated in FIG. 3 can be changed appropriately.

Figure 4:
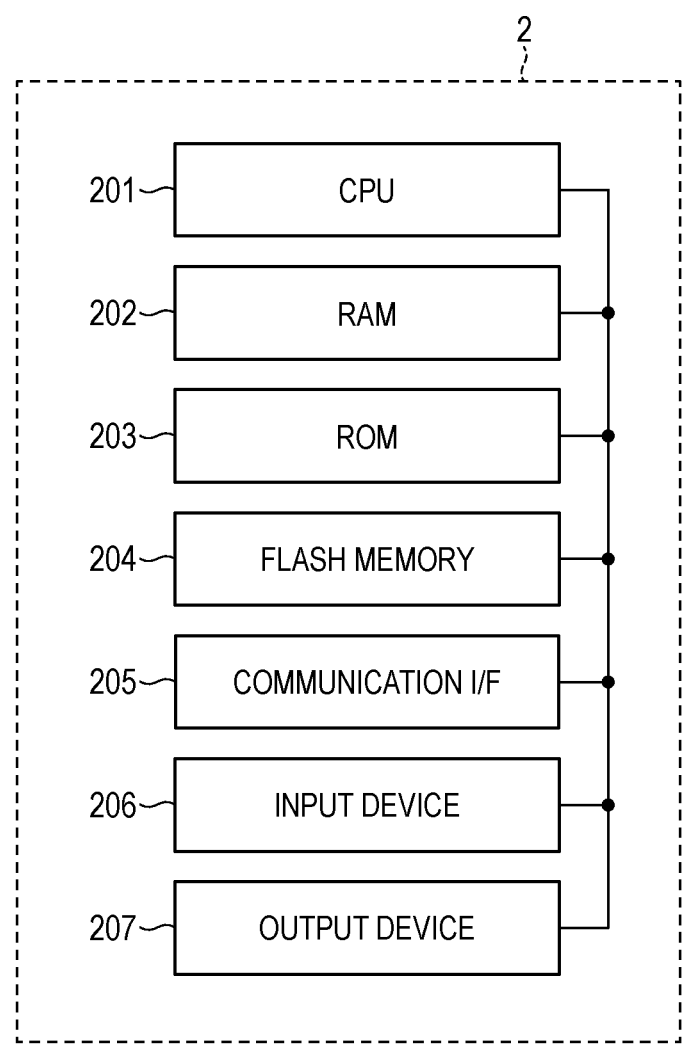
FIG. 4 is a block diagram illustrating a hardware configuration of an information communication terminal according to the first example embodiment.

FIG. 4 is a block diagram illustrating a hardware configuration example of the information communication terminal 2. The information communication terminal 2 includes a CPU 201, a RAM 202, a ROM 203, and a flash memory 204. The information communication terminal 2 also includes a communication I/F 205, an input device 206, and an output device 207. Each unit of the information communication terminal 2 is connected to each other via a bus, wiring, a driving device, or the like.

In FIG. 4, each unit constituting the information communication terminal 2 is illustrated as an integrated device, but some of these functions may be provided by an external device. For example, the input device 206 and the output device 207 may be external devices different from those constituting the functions of the computer including the CPU 201 or the like.

The CPU 201 is a processor that performs predetermined calculation in accordance with a program stored in the ROM 203, the flash memory 204, or the like, and also has a function of controlling each unit of the information communication terminal 2. The RAM 202 is composed of a volatile storage medium and provides a temporary memory area required for the operation of the CPU 201. The ROM 203 is composed of a non-volatile storage medium and stores necessary information such as a program used for the operation of the information communication terminal 2. The flash memory 204 is a storage device composed of a non-volatile storage medium for storing data transmitted and received to and from the walking environment determination device 1 and for storing a program for operating the information communication terminal 2.

The communication I/F 205 is a communication interface based on standards such as Bluetooth (registered trademark), Wi-Fi (registered trademark) or 4G and is a module for performing communication with other devices.

The input device 206 is a user interface used by the user 4 to operate the information communication terminal 2. Examples of the input device 206 include a mouse, a trackball, a touch panel, a pen tablet, a button, or the like.

The output device 207 is, for example, a display device. The display device is a liquid crystal display, an organic light emitting diode (OLED) display, or the like, and is used for displaying information, displaying a graphical user interface (GUI) for operation input, or the like. The input device 206 and the output device 207 may be integrally formed as a touch panel.

Note that the hardware configuration illustrated in FIG. 4 is an example, and other devices may be added or some devices may not be provided. Further, some devices may be replaced by other devices having similar functions. Further, some functions of the present example embodiment may be provided by other devices via a network, or some functions of the present example embodiment may be realized by being distributed among a plurality of devices. For example, the flash memory 204 may be replaced by a hard disk drive (HDD) or a cloud storage. Thus, the hardware configuration illustrated in FIG. 4 can be changed appropriately.

The server 3 is a computer having substantially the same hardware configuration as that illustrated in FIG. 4. Since the hardware configuration of the server 3 is substantially the same as that of the information communication terminal 2 except that the server 3 may not be portable, a detailed description thereof is omitted.

Figure 5:
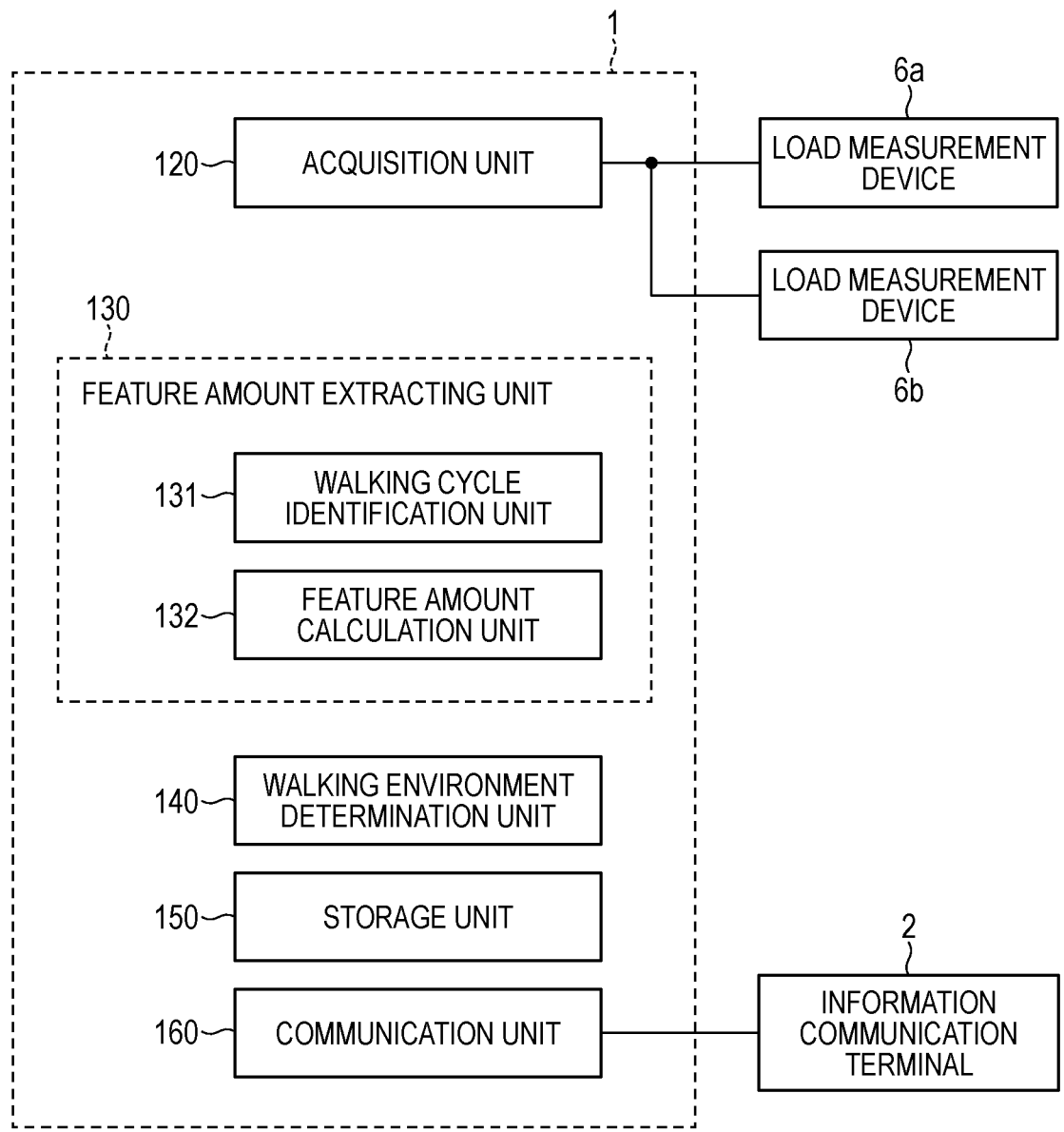
FIG. 5 is a functional block diagram of a walking environment determination device according to the first example embodiment.

FIG. 5 is a functional block diagram of the walking environment determination device 1 according to the present example embodiment. The walking environment determination device 1 includes an acquisition unit 120, a feature amount extracting unit 130, a walking environment determination unit 140, a storage unit 150, and a communication unit 160. The feature amount extracting unit 130 includes a walking cycle identification unit 131 and a feature amount calculation unit 132.

The CPU 101 loads a program stored in the ROM 103, the flash memory 104, or the like into the RAM 102 and executes the program. Thus, the CPU 101 realizes the functions of the feature amount extracting unit 130 and the walking environment determination unit 140. Further, the CPU 101 realizes the function of the acquisition unit 120 by controlling the sensor control device 106 based on the program. The CPU 101 realizes the function of the storage unit 150 by controlling the flash memory 104 based on the program. Further, the CPU 101 realizes the function of the communication unit 160 by controlling the communication I/F 105 based on the program. Specific processing performed by each of these units is described later.

In the present example embodiment, each function of the functional blocks illustrated in FIG. 5 is provided in walking environment determination device 1, but some functions of the functional blocks illustrated in FIG. 5 may be provided in the information communication terminal 2 or the server 3. That is, the above-described functions may be realized by any of the walking environment determination device 1, the information communication terminal 2, and the server 3, or may be realized by cooperation of the walking environment determination device 1, the information communication terminal 2, and the server 3.

Figure 6:
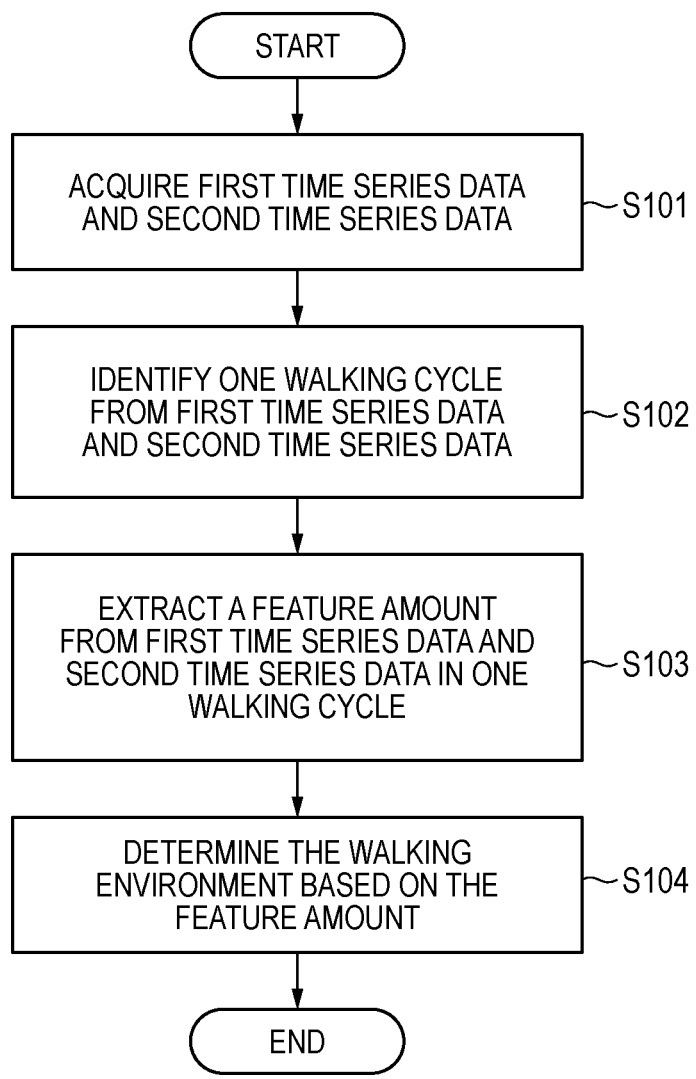
FIG. 6 is a flowchart illustrating an example of a walking environment determination process performed by the walking environment determination device according to the first example embodiment.

FIG. 6 is a flowchart illustrating an example of a walking environment determination process performed by the walking environment determination device 1 according to the present example embodiment. The process of FIG. 6 is performed when the walking environment determination device 1 detects walking, for example, when the user 4 is walking. Alternatively, the process of FIG. 6 may be always performed unrelated to whether or not the user 4 is walking, or may be performed at predetermined time intervals.

In step S101, the acquisition unit 120 controls the load measurement devices 6a and 6b to acquire time series data of load from the load measurement devices 6a and 6b. That is, the acquisition unit 120 acquires the first time series data from the load measurement device 6a and acquires the second time series data from the load measurement device 6b. Thus, the acquisition unit 120 can acquire time changes in the load caused by walking of the user 4. The acquired time series data of the load is converted into digital data and then stored in the storage unit 150. In addition, the time series data of the load is referred to as walking data because it indicates the feature of walking. The walking data can be used not only for the walking environment determination of the present example embodiment but also for the gait analysis or personal identification of the user 4.

Figure 7:
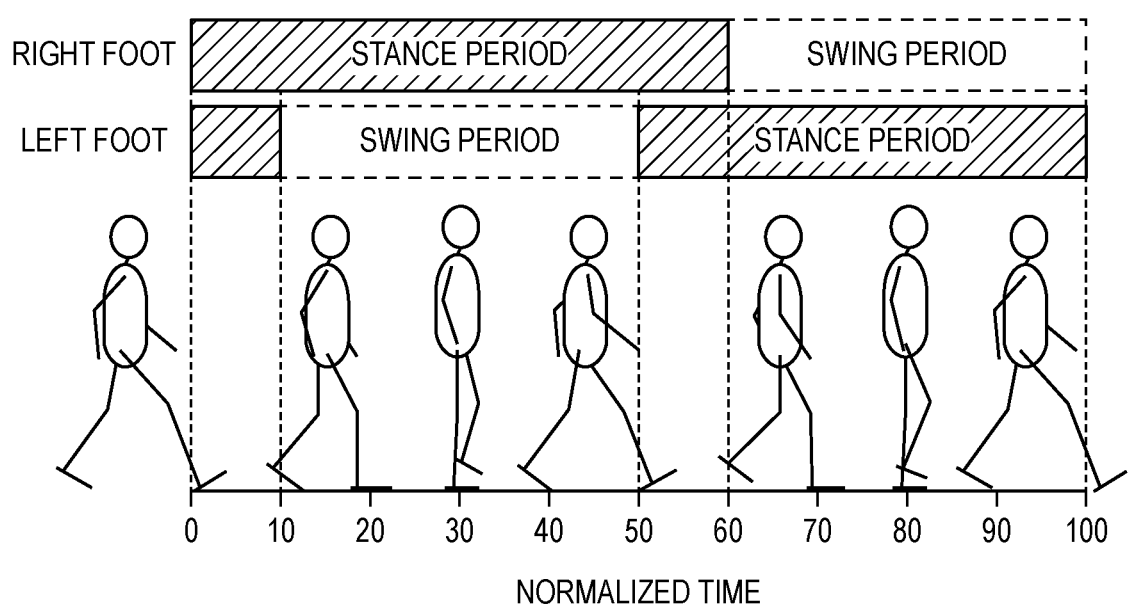
FIG. 7 is a conceptual diagram illustrating a walking cycle.

Here, in order to sufficiently acquire features included in walking, it is desirable that time series data of the load include data in a period corresponding to at least one walking cycle. One walking cycle is described with reference to FIG. 7. FIG. 7 is a conceptual diagram illustrating a walking cycle. FIG. 7 schematically illustrates motion of the right foot and the left foot of the user 4 for one walking cycle. The normalized time in the figure indicates the time normalized so that the length of one walking cycle is 100. That is, the normalized time 0 in the figure is the moment at which the right foot lands, the normalized time 50 in the figure is the moment at which the left foot lands, and the normalized time 100 in the figure is the moment at which the right foot lands again. A period from the normalized time 0 to 100 is one walking cycle.

Further, a period in which the foot lands is referred to as a stance period, and a period in which the foot leaves the ground is referred to as a swing period. More specifically, for example, the stance period of the right foot is a period from the moment at which the heel of the right foot lands (at the time of landing) to the moment at which the toe of the right foot leaves the ground (at the time of leaving), and generally occupies a period of about 60% of one walking cycle. The swing period of the right foot is a period from the moment when the toe of the right foot leaves the ground to the moment when the heel of the right foot lands, and generally occupies a period of about 40% of one walking cycle. As illustrated in FIG. 7, during walking, the stance period and the swing period are alternately repeated. Further, the phase of the stance period and the phase of the swing period are opposite between the right foot and the left foot.

In step S102, the walking cycle identification unit 131 identifies one walking cycle of the first time series data and the second time series data. Since substantially the same motion is repeated for each step during walking, one walking cycle can be identified by detecting periodicity of time series data. For example, one walking cycle can be identified based on the appearance time of the peak or dip of the time series data, the frequency of the peak included in the frequency spectrum acquired by Fourier-transforming the time series data, or the like.

In step S103, the feature amount calculation unit 132 extracts a feature amount indicating walking environment from the first time series data and the second time series data in at least one walking cycle. The extracted feature amount is stored in the storage unit 150. The extraction of the feature amount is described with a specific example.

Figure 8:
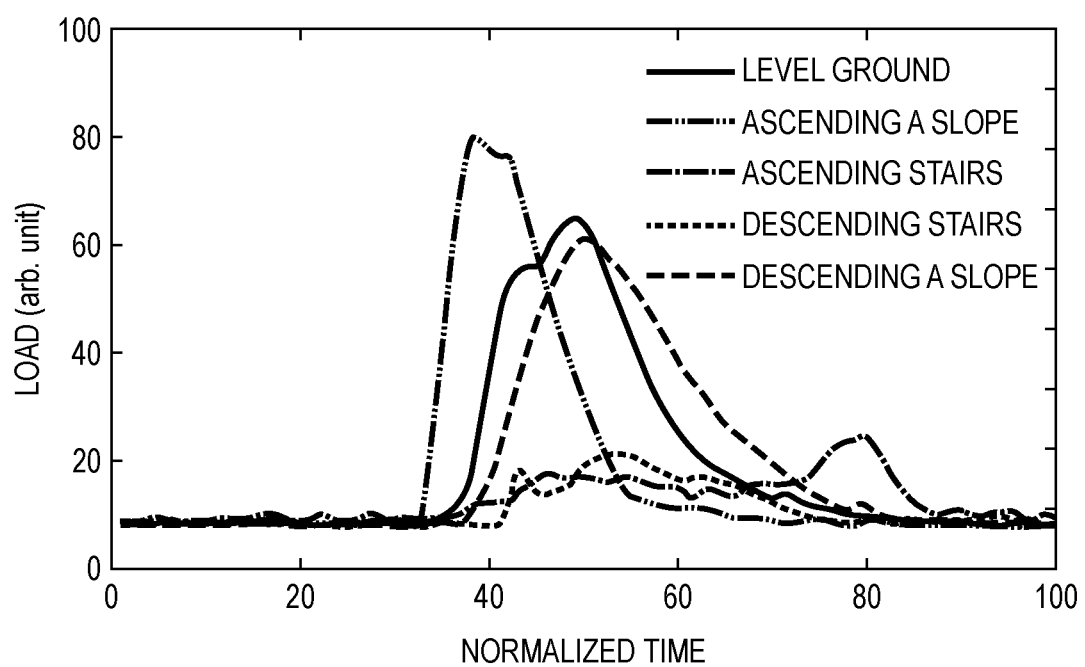
FIG. 8 is a graph illustrating an example of time series data of load.
Figure 9:
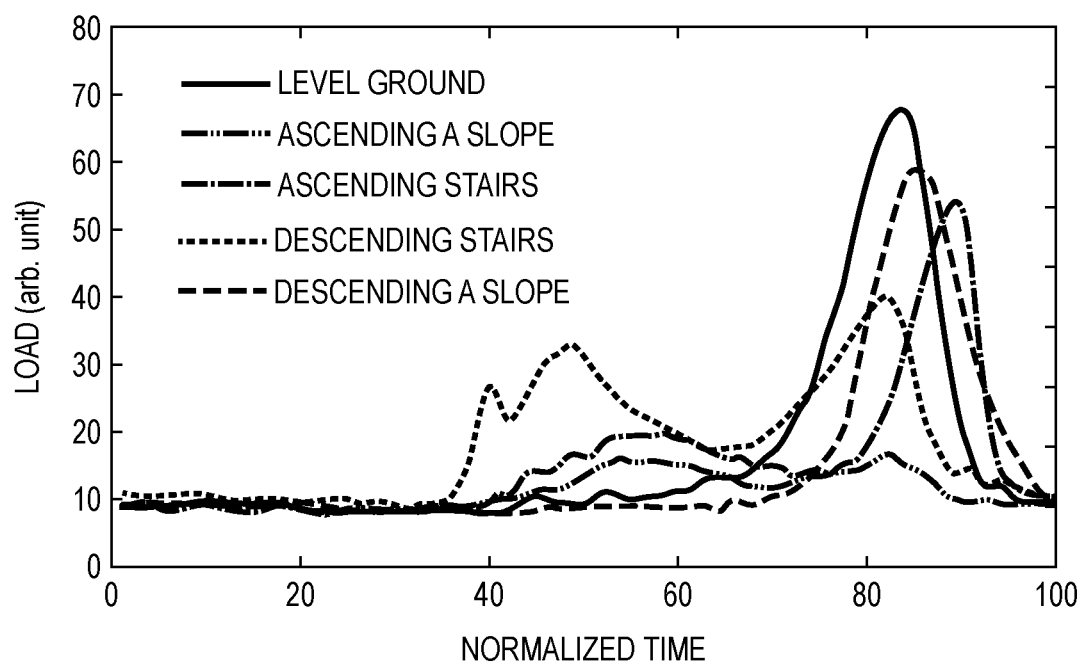
FIG. 9 is a graph illustrating an example of time series data of load.

FIG. 8 is a graph illustrating an example of the first time series data of load acquired by the load measurement device 6a in one walking cycle. FIG. 9 is a graph illustrating an example of the second time series data of load acquired by the load measurement device 6b in one walking cycle. The horizontal axis of FIG. 8 and FIG. 9 represents the normalized time in one walking cycle, and the vertical axis of FIG. 8 and FIG. 9 represents load in arbitrary units. Note that, since the value of the normalized time may change depending on the definition of the start point and the end point of the walking cycle, in FIG. 8 and FIG. 9, the value of the normalized time does not always coincide with that of FIG. 7.

In FIG. 8 and FIG. 9, five graphs of different line types illustrate differences in time fluctuation of load due to differences in the walking environment of the user 4. "level ground" in the graph indicates a case where the user 4 is walking on level ground. "ascending stairs" and "descending stairs" in the graph indicate the case where the user 4 is ascending stairs and the case where the user 4 is descending stairs, respectively. "ascending a slope" and "descending a slope" in the graph indicate the case where the user 4 is ascending a slope and the case where the user 4 is descending a slope, respectively.

As can be understood from FIG. 8 and FIG. 9, the appearance time of the peak is significantly different depending on the difference in walking environment. In addition, a difference in size of the peak is also seen due to differences in walking environment. Therefore, the walking environment of the user 4 can be determined by extracting the feature amount from the first time series data and the second time series data in one walking cycle. Specific examples of the feature amount extracted in this process include appearance time of the peak and size of the peak. The feature amount extracted in this process may include a plurality of elements, in other words, the feature amount extracted in this process may be a feature amount vector.

In step S104, the walking environment determination unit 140 determines the walking environment based on the extracted feature amount. Thus, the walking environment determination unit 140 can determine a walking environment such as whether a location where the user 4 is walking on level ground or a location other than level ground such as stairs or a slope.

In the process of determining the walking environment from the feature amount performed by the walking environment determination unit 140, a trained model generated in advance by machine learning and stored in the storage unit 150 is used. Examples of algorithms used for machine learning include decision trees, random forests, support vector machines, neural networks, deep learning, logistic regression, k-nearest neighbor algorithm (K-NN), ensemble learning for classification method, discriminant analysis, or the like. Further, generation of a trained model by machine learning (training process) is performed in the walking environment determination device 1, the information communication terminal 2, or the server 3 using sample data prepared in advance.

The training process for generating a trained model used for a determination of a walking environment in step S104 is described in more detail. This process is performed in advance in the walking environment determination device 1, the information communication terminal 2, or the server 3 prior to the process of FIG. 6. In the description of the present example embodiment, it is assumed that the training process is performed in the server 3.

Figure 10:
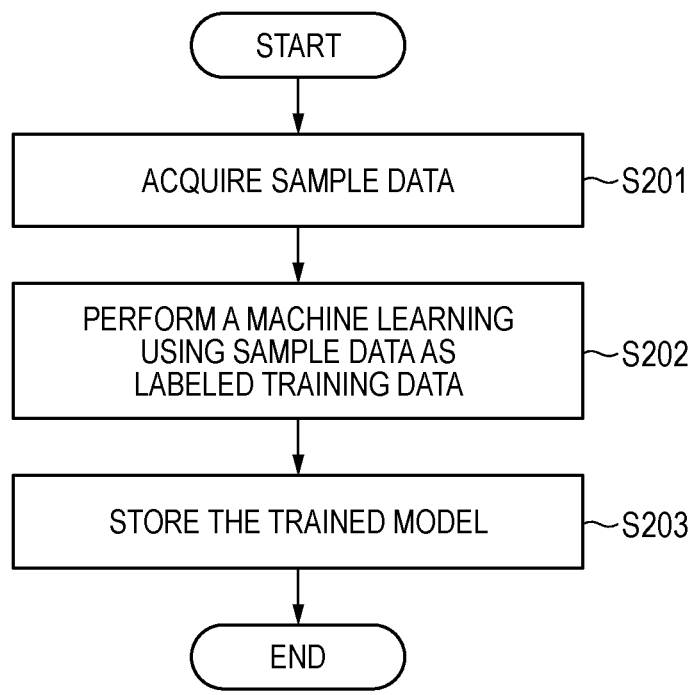
FIG. 10 is a flowchart illustrating an example of a training process performed by the server according to the first example embodiment.

FIG. 10 is a flowchart illustrating an example of training process performed by the server 3 according to the present example embodiment. The process of FIG. 10 is performed prior to the walking state determination process at the time of shipment from a factory, calibration before the user 4 uses the walking environment determination device 1, or the like.

In step S201, the server 3 acquires sample data for training. This sample data may be, for example, one in which a label indicating a walking state is associated with a feature amount vector acquired by the processing from step S101 to step S103. The label indicating the walking state is attached in advance by the user 4, the administrator of the walking environment determination system, or the like. More specifically, by causing the user 4 to actually walk on various places such as level ground and a slope and the walking environment determination device 1 to acquire data and input the walking place, sample data in which the feature amount vector and the label are associated with each other can be created.

In step S202, the server 3 performs machine learning on the sample data as labeled training data. As a result, a trained model is generated in which an appropriate walking state is output with respect to the input of the feature amount vector.

In step S203, the server 3 stores the trained model in a storage device. Thereafter, the server 3 provides the trained model to the walking environment determination device 1. Specifically, the server 3 transmits the trained model to the information communication terminal 2. The information communication terminal 2 causes the walking environment determination device 1 to install the received trained model as software for processing in the walking environment determination unit 140.

FIG. 11 is a table schematically illustrating the correspondence relation between a feature vector and a walking state label acquired by the present training process. As illustrated in FIG. 11, a walking state label such as "level ground" and "ascending stairs" is determined corresponding to a feature amount vector including "time of a peak of first time series data", "size of a peak of first time series data", "time of a peak of second time series data", and the like. In other words, the trained model acquired by the training process has a function of outputting a walking state label as a response variable when a feature amount vector is input as an explanatory variable. Note that, generation of the trained model by the present training process may be performed individually for each subject of the walking environment determination, or may be common to subjects.

Example 1

A result of actually determining the walking environment using the walking environment determination system of the first example embodiment is described as an example 1. In the present example, walking data including five types of walking environments of "level ground", "ascending stairs", "descending stairs", "ascending a slope", and "descending a slope" were acquired. A large number of feature amount vectors were extracted from these walking data to create data groups for training and validation. In the present example, cross-validation was performed using this data group. Specifically, randomly selected some data in the data group was used as validation data, and the remaining data was used as training data. That is, a trained model was generated using training data of some data group, and the recognition rate of the trained model was validated using the remaining data. The number of divisions of cross-validation was 10.

Figure 12:
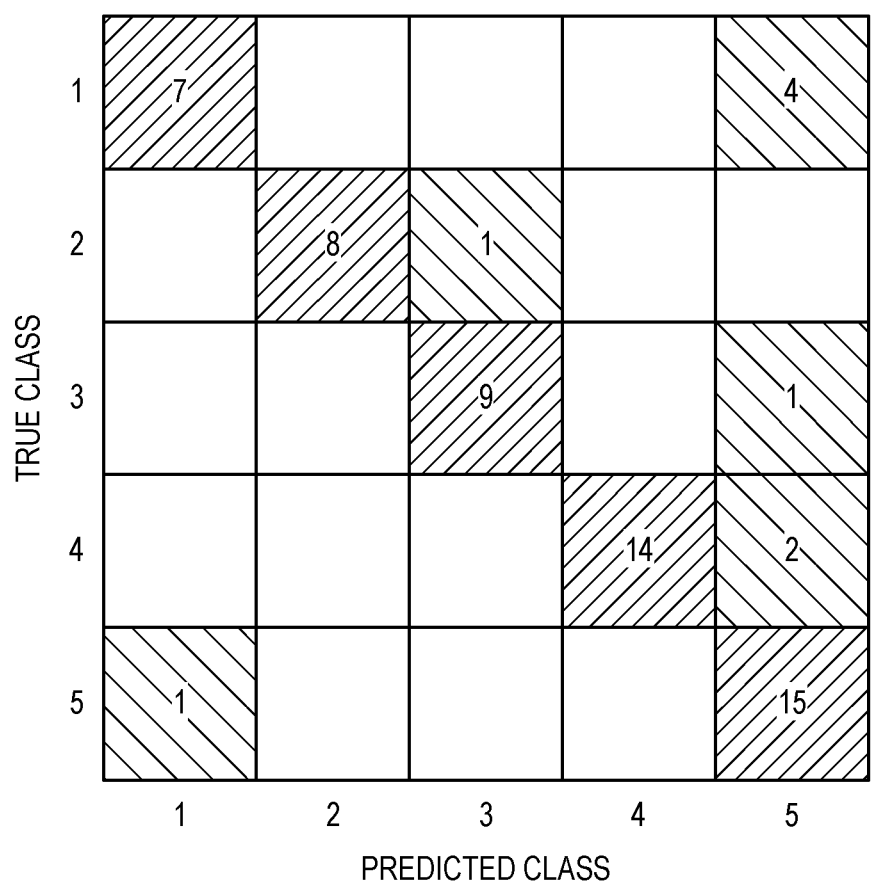
FIG. 12 is a table illustrating a result of cross-validation.

FIG. 12 is a table illustrating a result of cross-validation using this data group. The "predicted class" in the table is a class of the walking environment determined by the walking environment determination system of the first example embodiment, and the "true class" is a class indicating the walking environment of a place where the subject actually walks. The numbers "1", "2", "3", "4", and "5" of the classes in the table indicate "level ground", "ascending stairs", "descending stairs", "ascending a slope", and "descending a slope", respectively. For example, in the prediction performed by the walking environment determination system for 16 data groups whose true class is "4 (ascending a slope)", the walking environment determination system correctly predicted the class "4" for 14 out of 16 data groups.

In contrast, an incorrect class "5" was predicted for two of 16 data groups. As illustrated in FIG. 12, in the walking environment system of the first example embodiment, the walking environment could be determined at a high correct rate of about 85%. As described above, according to the present example embodiment, the walking environment determination device 1 and the walking environment determination system capable of determining the walking environment with high accuracy are provided.

As described above, according to the present example embodiment, the information processing device capable of suitably extracting the feature amount used for determining the walking environment is provided. Further, the walking environment determination device 1 and the walking environment determination system capable of determining the walking environment with high accuracy are provided by using the feature amount extracted by the information processing device.

The walking environment determination system of the present example embodiment can determine whether or not the location where the user 4 is walking is level ground. Hereinafter, an example of application of the walking environment determination system of the present example embodiment is described.

Generally, the walking pattern of a human is different between level ground and ground other than the level ground. Therefore, when the analysis of the walking pattern of the user 4 (gait analysis) is performed, the walking data of a place other than the level ground such as a slope or stairs may be excluded. In such a case, there is a need to determine from the walking data whether or not the location where the user 4 is walking is the level ground. By determining the walking environment using the walking environment determination system of the present example embodiment, the walking data of a place other than the level ground can be easily excluded from the walking data for gait analysis. In addition, the storage capacity and the communication amount of the walking data can be reduced by performing the data processing for deleting the walking data of a place other than the level ground at the time of acquiring the walking data. Alternatively, the power consumption of the walking environment determination device 1 can be reduced by controlling the walking environment determination device 1 so as not to acquire walking data of a place other than the level ground.

Second Example Embodiment

A walking environment determination system of the present example embodiment differs from that of the first example embodiment in that the time series data acquired from the two load measurement devices 6a and 6b are added together and then the feature amount is extracted. Hereinafter, differences from the first example embodiment are mainly described, and description of common portions is omitted or simplified.

Figure 13:
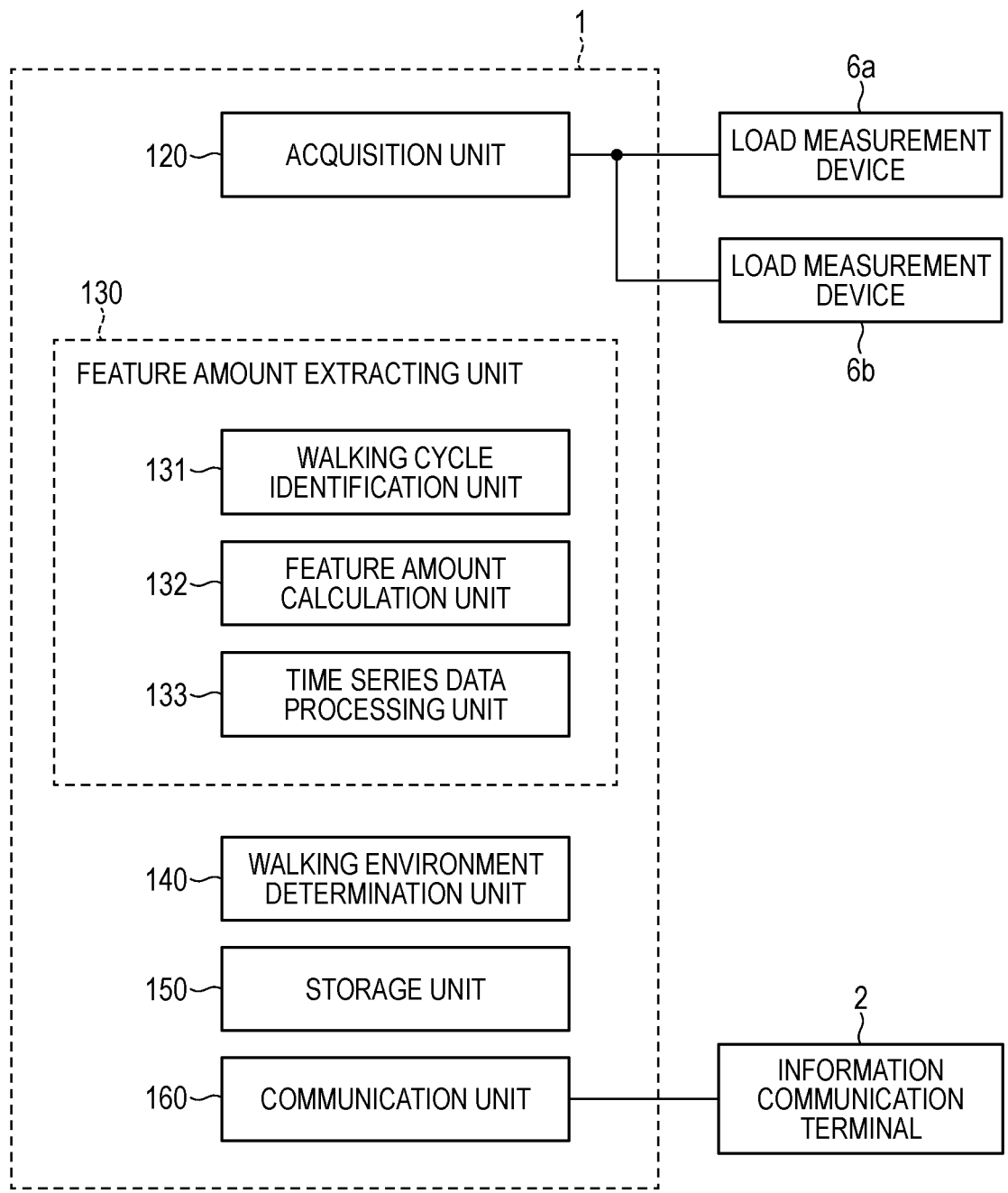
FIG. 13 is a functional block diagram of a walking environment determination device according to a second example embodiment.

FIG. 13 is a functional block diagram of the walking environment determination device 1 according to the present example embodiment. The feature amount extracting unit 130 of the walking environment determination device 1 further includes a time series data processing unit 133 in addition to the configuration described in the first example embodiment.

Figure 14:
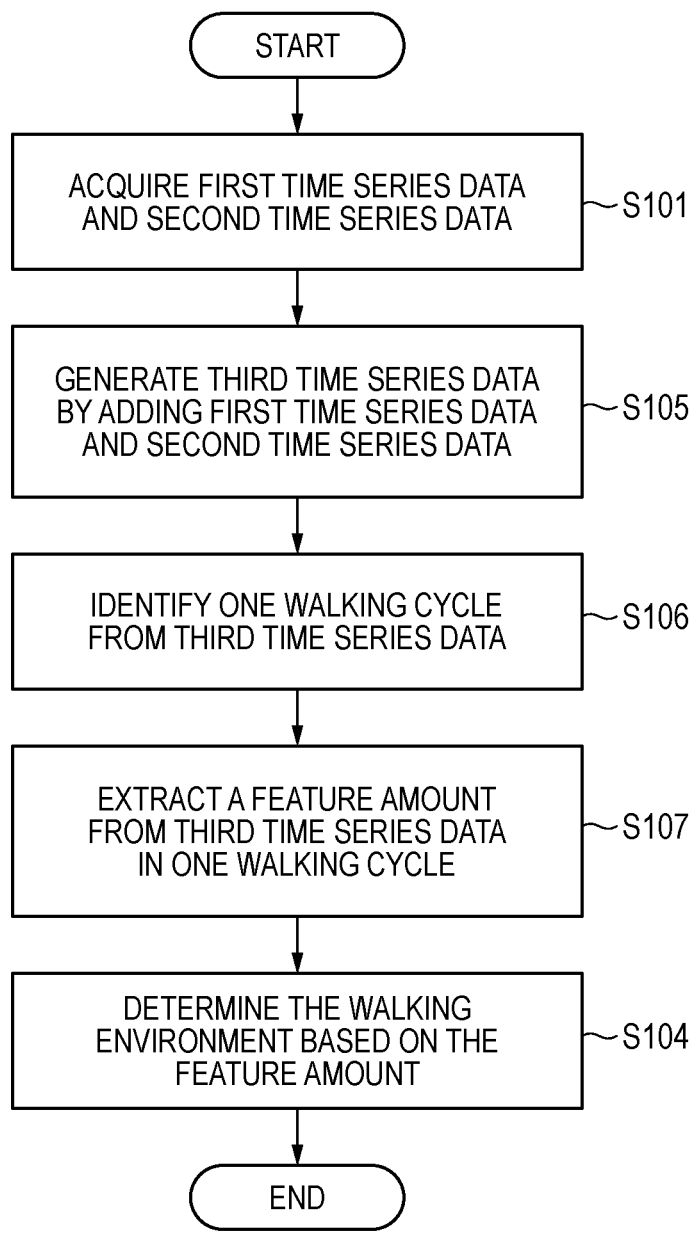
FIG. 14 is a flowchart illustrating an example of a walking environment determination process performed by the walking environment determination device according to the second example embodiment.

FIG. 14 is a flowchart illustrating an example of walking environment determination process performed by the walking environment determination device 1 according to the present example embodiment. The same steps as those in FIG. 6 are denoted by the same reference numerals, and description common to those in FIG. 6 is omitted or simplified.

In step S105, the time series data processing unit 133 generates third time series data by adding first time series data acquired from the load measurement device 6a and second time series data acquired from the load measurement device 6b. In this process, digital data of load at the same time in the first time series data and the second time series data are added together. Thus, the third time series data including the characteristic based on the load output from both the load measurement devices 6a and 6b can be acquired.

The order and contents of step S101 and step S105 can be changed appropriately. Step S101 and Step S105 may be performed simultaneously or as a series of processes. For example, these processes may be modified to a process in which the time series data are added together to generate and store the third time series data when the time series data are acquired from the load measurement devices 6a and 6b. In this case, the first time series data and the second time series data need not be stored. These processes may be modified to a process of adding analog signals measured by the load measurement devices 6a and 6b in a circuit before AD conversion. In this case, the addition is completed before the acquisition unit 120 acquires the data. In this processing method, the number of AD conversion processes is reduced.

In step S106, the walking cycle identification unit 131 identifies one walking cycle of the third time series data. In step S107, the feature amount calculation unit 132 extracts a feature amount indicating the walking environment from the third time series data in at least one walking cycle. The extracted feature amount is stored in the storage unit 150. The extraction of the feature amount is described with reference to a specific example.

Figure 15:
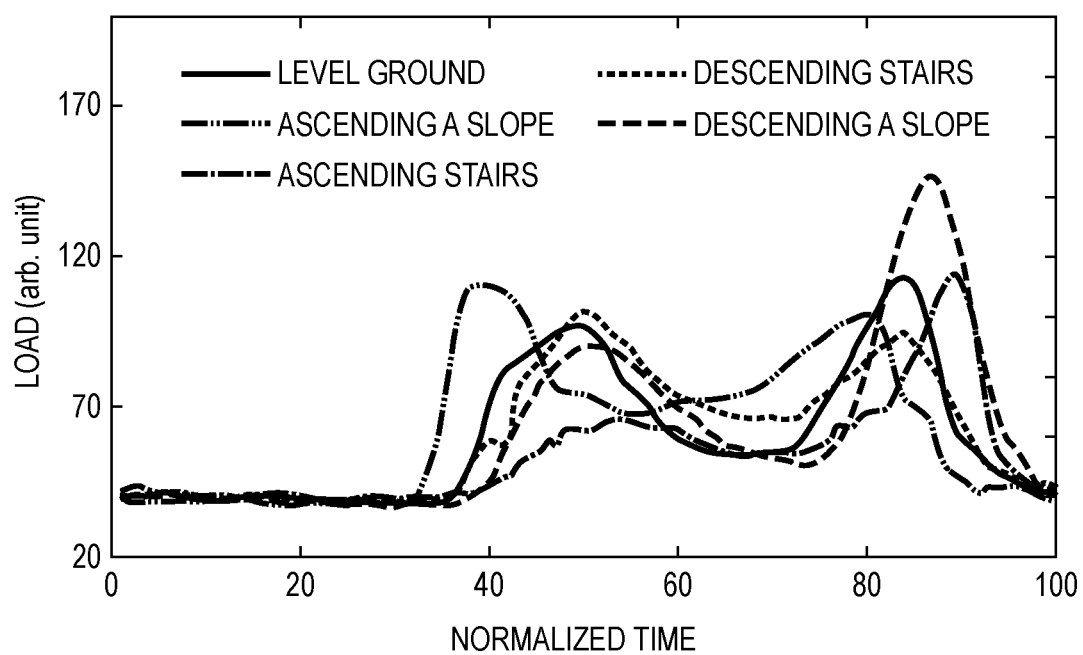
FIG. 15 is a graph illustrating an example of time series data of load.

FIG. 15 is a graph illustrating an example of the third time series data that is a total value of load acquired by the load measurement devices 6a and 6b. The notation of the graph is the same as that in FIG. 8 and FIG. 9, so that the description thereof is omitted.

As can be understood from FIG. 15, there are two peaks in each graph. Hereinafter, these two peaks may be referred to as P1 and P2 in order from the earlier time. The appearance time of the peaks P1 and P2 are significantly different in accordance with the difference in walking environment. In addition, a difference in the size of the peaks P1 and P2 is also seen due to a difference in walking environment. Therefore, the walking environment of the user 4 can be determined by extracting the feature amount from the third time series data in one walking cycle. Specific examples of the feature amount extracted in this process include the appearance time of the peaks P1 and P2, the size of the peaks P1 and P2, and the time difference between P1 and P2. The feature amount extracted in this process may include a plurality of elements, in other words, the feature amount extracted in this process may be a feature amount vector.

In step S104, the walking environment determination unit 140 determines the walking environment using the trained model in the same manner as in the first example embodiment. FIG. 16 is a table schematically illustrating a correspondence relation between a feature amount vector and a walking state label acquired by training process for generating a trained model according to the present example embodiment. As illustrated in FIG. 16, walking state labels such as "level ground" and "ascending stairs" are determined corresponding to feature amount vectors including "time of P1", "size of P1", "time of P2", "size of P2", "time difference between P1 and P2 (difference between appearance time of P2 and appearance time of P1), and the like. By extracting feature amounts based on a plurality of peaks in this way, many features can be extracted, and determination accuracy can be improved.

Example 2

A result of actually determining the walking environment using the walking environment determination system of the second example embodiment is described as example 2. In the present example, walking data including five types of walking environments of "level ground", "ascending stairs", "descending stairs", "ascending a slope", and "descending a slope" were acquired. A large number of feature amount vectors were extracted from these walking data to create data groups for training and validation. In the present example, cross-validation was performed in the same manner as in example 1 using this data group. Note that, the number of divisions of cross-validation was 10.

Figure 17:
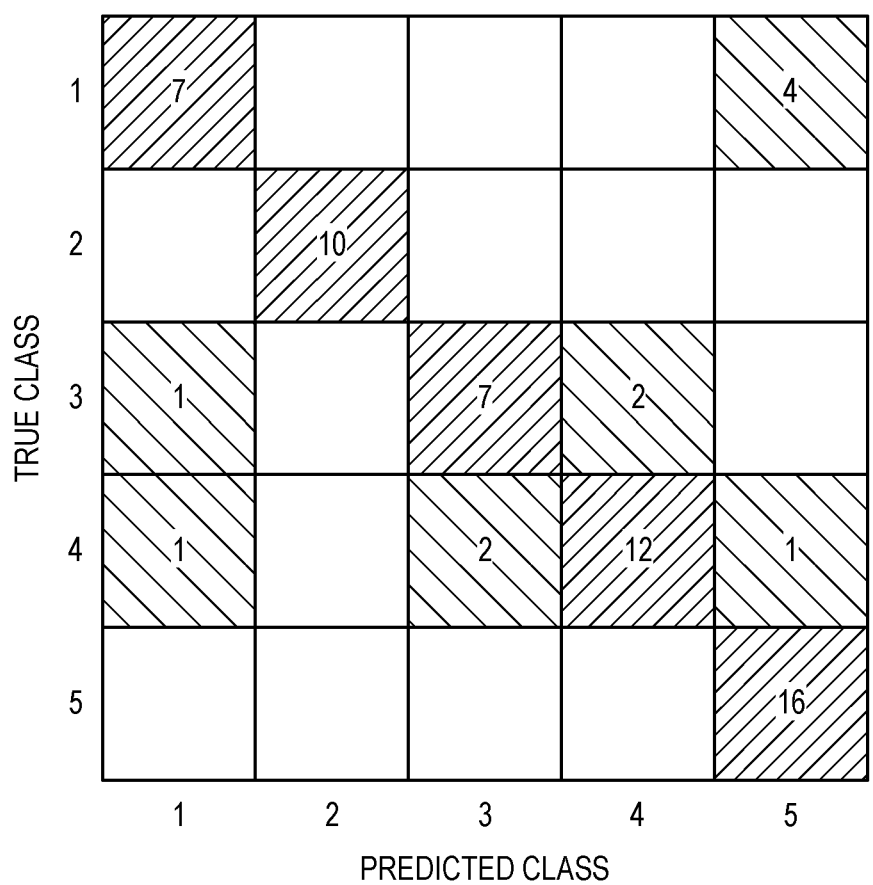
FIG. 17 is a table illustrating a result of cross-validation.

FIG. 17 is a table illustrating results of cross-validation using this data group. The description in the table is the same as that in FIG. 12, so that the description thereof is omitted. As illustrated in FIG. 17, in the walking environment system of the first example embodiment, the walking environment could be determined at a high correct rate of about 83%. As described above, the present example embodiment also provides the walking environment determination device 1 and the walking environment determination system capable of determining the walking environment with high accuracy as in the first example embodiment.

As described above, in the present example embodiment, as in the first example embodiment, the information processing device capable of suitably extracting the feature amount used for the determination of the walking environment is provided. Further, the walking environment determination device 1 and the walking environment determination system capable of determining the walking environment with high accuracy by using the feature amount extracted by the information processing device are provided.

Third Example Embodiment

A walking environment determination system of the present example embodiment is different from that of the first example embodiment in that the walking environment determination system has a function of measuring walking data for gait analysis and a function of switching two modes with different power consumption. Hereinafter, differences from the first example embodiment are mainly described, and description of common portions is omitted or simplified.

Figure 18:
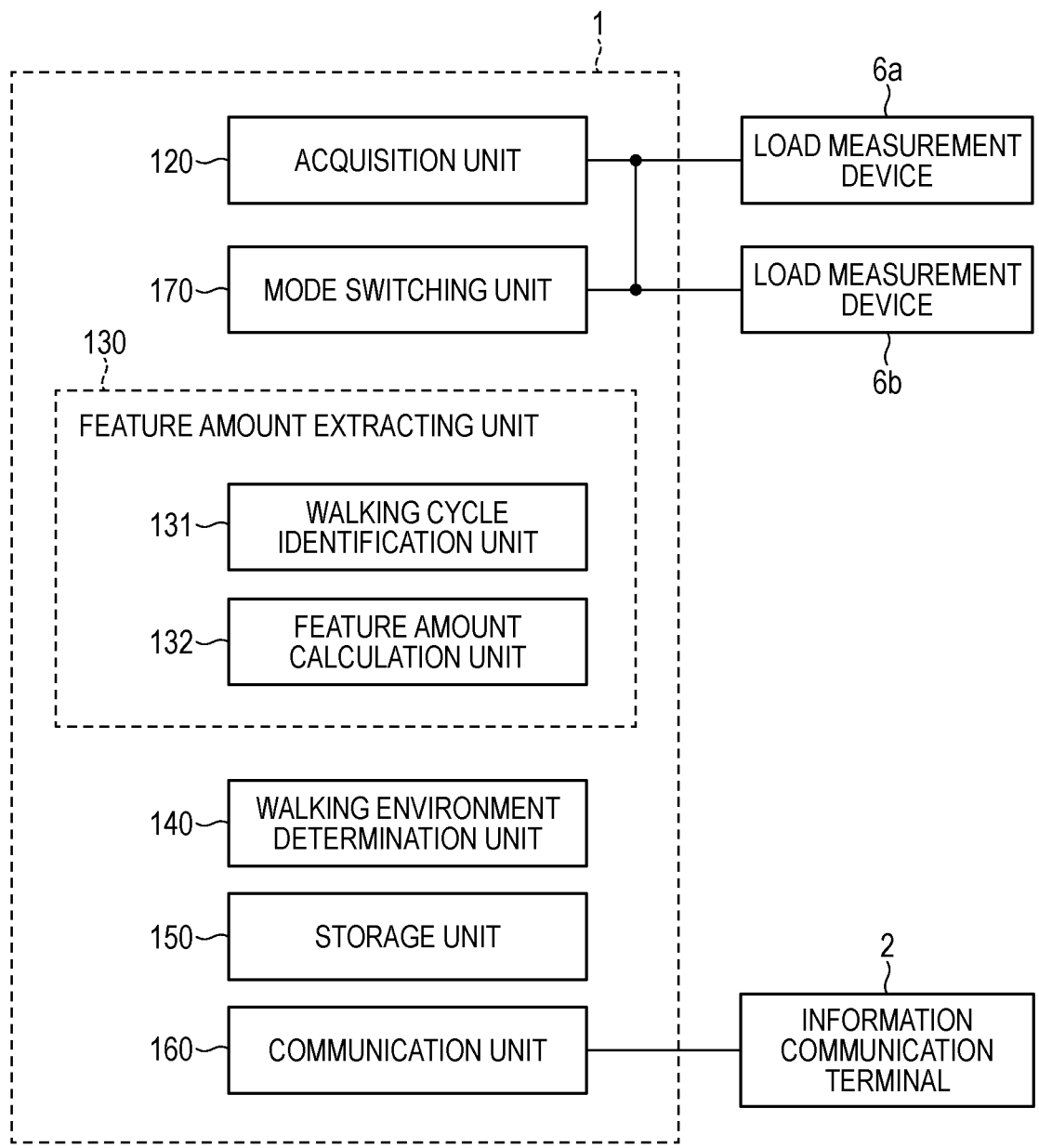
FIG. 18 is a functional block diagram of a walking environment determination device according to a third example embodiment.

FIG. 18 is a functional block diagram of the walking environment determination device 1 according to the present example embodiment. The walking environment determination device 1 further includes a mode switching unit 170 in addition to the elements described in the first example embodiment. The load measurement devices 6a and 6b of the present example embodiment can operate in a normal mode and a power saving mode in which power consumption thereof is smaller than that in the normal mode. The mode switching unit 170 has a function of controlling the operation mode of the load measurement devices 6a and 6b to the normal mode or the power saving mode. The normal mode may be referred to as the first mode more generally, and the power saving mode may be referred to as the second mode more generally.

The difference between the normal mode and the power saving mode may be a difference in types of processes that the load measurement devices 6a and 6b can perform. For example, the power saving mode may reduce power consumption by stopping functions of some devices in the load measurement devices 6a and 6b. Alternatively, the difference between the normal mode and the power saving mode may be a difference in sampling rate. In this case, the power consumption of the sensors in the load measurement devices 6a and 6b can be reduced by reducing the frequency of acquiring data in the power saving mode as compared with the normal mode.

The CPU 101 realizes the function of the mode switching unit 170 by loading a program stored in the ROM 103, the flash memory 104, or the like into the RAM 102 and executing the program. The function of the mode switching unit 170 may be provided in the information communication terminal 2 or the server 3, or may be provided in the load measurement devices 6a and 6b.

Figure 19:
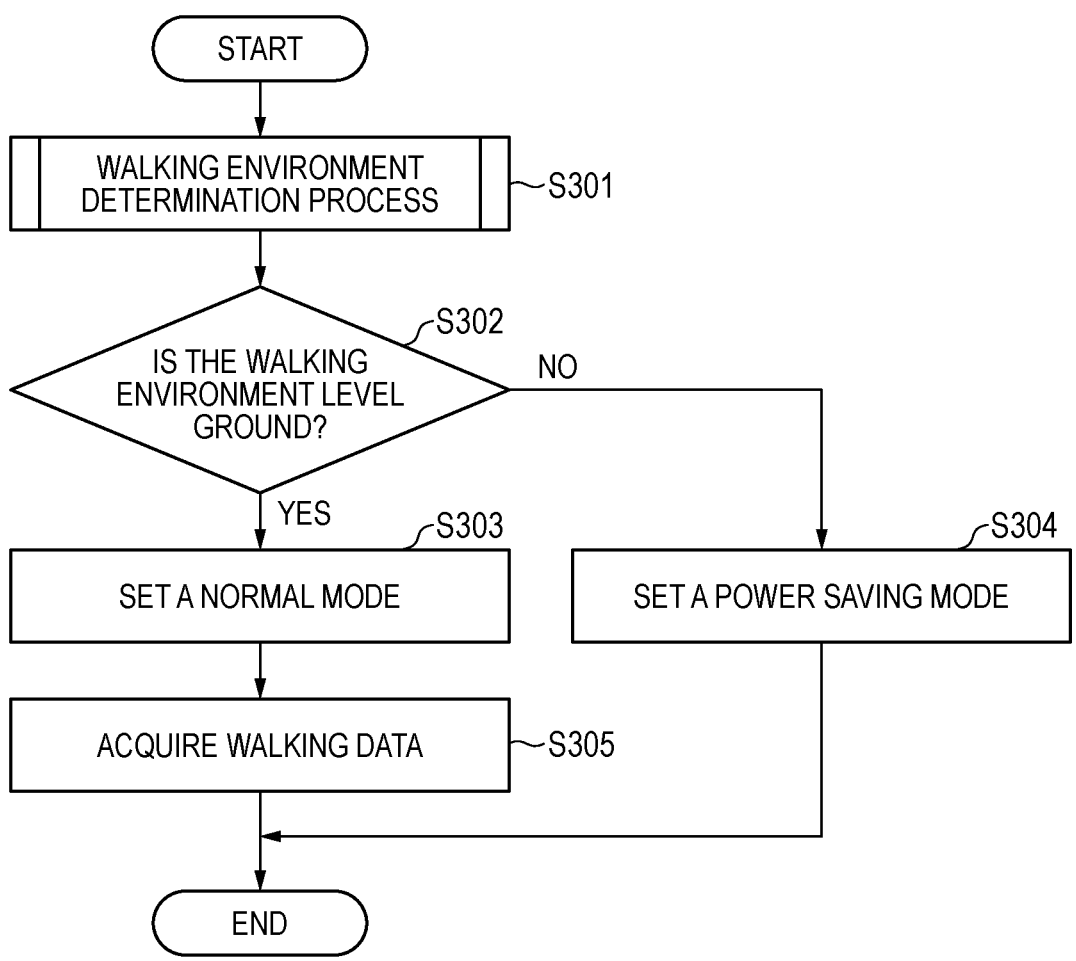
FIG. 19 is a flowchart illustrating an example of a mode switching process performed by the walking environment determination device according to the third example embodiment.

FIG. 19 is a flowchart illustrating an example of a mode switching process performed by the walking environment determination device 1 according to the present example embodiment. The process of FIG. 19 is performed when the walking environment determination device 1 detects walking, for example, when the user 4 is walking. Alternatively, the process of FIG. 19 may be always performed unrelated to whether or not the user 4 is walking, or may be performed at predetermined time intervals.

In step S301, each unit of the walking environment determination device 1 performs walking environment determination process. This walking environment determination process is the same as steps S101 to S104 in FIG. 6, and a description thereof is omitted.

In step S302, the mode switching unit 170 determines whether or not the walking environment of the user 4 is level ground based on the result of the walking environment determination process. If it is determined that the walking environment is level ground (YES in step S302), the process proceeds to step S303. If it is determined that the walking environment is not level ground (NO in step S302), the process proceeds to step S304.

In step S303, the mode switching unit 170 controls the operation mode of the load measurement devices 6a and 6b to the normal mode. Thereafter, in step S305, the acquisition unit 120 controls the load measurement devices 6a and 6b to acquire walking data for gait analysis.

In step S304, the mode switching unit 170 controls the operation mode of the load measurement devices 6a and 6b to the power saving mode, and the process ends. When the walking data for gait analysis can be acquired even in the power saving mode, the same processing as in step S305 may be performed after step S304.

In order to properly perform gait analysis, it is desirable to use walking data in which the walking environment is level ground. In contrast, walking data acquired in a walking environment other than level ground is often not so effective for gait analysis. Therefore, the walking environment determination device 1 of the present example embodiment can acquire walking data for gait analysis in the normal mode when the walking environment is level ground, and reduces power consumption by switching to the power saving mode when the walking environment is not level ground. Therefore, it is possible to achieve both appropriate acquisition of walking data and low power consumption.

As described above, the walking environment determination 1 of the present example embodiment can reduce power consumption by controlling the load measurement devices 6*a* and 6*b* to be in the power saving mode when the walking environment is not level ground, in addition to the same effects as those of the first example embodiment. In a case where the load measurement devices 6*a* and 6*b* are provided in the shoe 5 or the like of the user 4 as in the present example embodiment, the power capacity of the battery 107 for driving the load measurement devices 6*a* and 6*b* cannot be increased so much. Therefore, reduction in power consumption according to the present example embodiment is effective.

Note that, in the example described above, although the load measurement devices 6*a* and 6*b* to switch the operation mode is described above, in the case where the walking environment determination device 1 has a configuration that may operate in the normal mode or the power saving mode, the walking environment determination device 1 may switch an operation mode. Specifically, the walking environment determination device 1 may acquire data from the load measurement devices 6*a* and 6*b* in the normal mode, and may not acquire data or reduce the acquisition frequency in the power saving mode. In this case, power consumption of the walking environment determination device 1 can be reduced.

In the above example, the function of the mode switching unit 170 is added to the configuration of the first example embodiment, but the function of the mode switching unit 170 may be added to the configuration of the second example embodiment.

The device or system described in the above example embodiments can also be configured as in the following fourth example embodiment.

Fourth Example Embodiment

Figure 20:
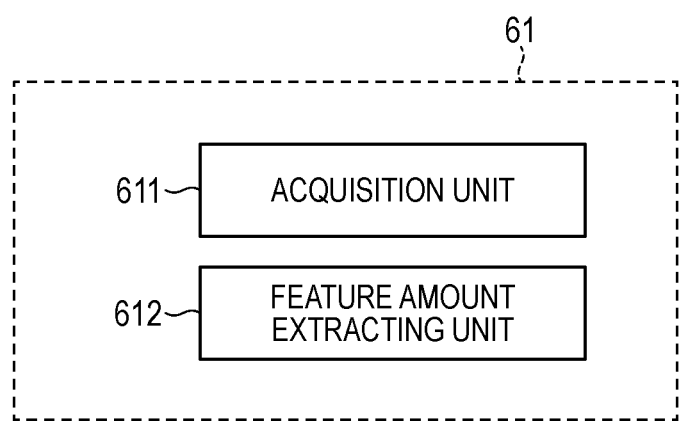
FIG. 20 is a functional block diagram of an information processing device according to a fourth example embodiment.

FIG. 20 is a functional block diagram of the information processing device 61 according to the fourth example embodiment. The information processing device 61 includes an acquisition unit 611 and a feature amount extracting unit 612. The acquisition unit 611 acquires load information based on a load applied to a load measurement device from a sole of a user. The feature amount extracting unit 612 extracts a feature amount indicating a walking environment from time series data in at least one walking cycle included in the load information.

According to the present example embodiment, there is provided an information processing device 61 capable of suitably extracting a feature amount used for determining a walking environment.

Modified Example Embodiments

The present invention is not limited to the example embodiments described above, and may be suitably modified within the scope of the present invention. For example, an example in which a part of the configuration of one example embodiment is added to another example embodiment or an example in which a part of the configuration of one example embodiment is replaced with another example embodiment is also an example embodiment of the present invention.

Although the walking environment determination process is performed inside the walking environment determination device 1 in the above-described example embodiment, this function may be provided in the information communication terminal 2. In this case, the information communication terminal 2 functions as a walking environment determination device.

In the example embodiment described above, the time series data of the load is acquired from the two load measurement devices, but the number and arrangement and the like of the load measurement devices are not limited thereto. For example, the number of load measurement devices may be one or three or more. When there is one load measurement device, the amount of data to be acquired is reduced, so that the amount of data to be processed may be reduced. When the number of load measurement devices is three or more, more information can be acquired, so that the accuracy of determining the walking environment may be improved.

In the above-described example embodiment, although the load measurement device is a load cell or the like and acquires a local load on the sole of the user 4, the load measurement device may be configured to acquire a load distribution over a wide range of the sole. For example, the load measurement device may have a configuration in which a large number of load measurement devices are arranged in the shoe 5, or a configuration in which a seat sensor in which a large number of load detecting elements are two-dimensionally arranged is arranged in the shoe 5 may be employed. In these cases, since the time series data of the load distribution of the sole of the user 4 can be acquired, and more information can be acquired, the accuracy of determining the walking environment may be improved.

A processing method in which a program for operating the configuration of the above-described example embodiments is recorded in a storage medium so as to implement the functions of the above-described example embodiments, the program recorded in the storage medium is read as code, and the program is executed in a computer is also included in the scope of each example embodiment. That is, a computer-readable storage medium is also included in the scope of the example embodiments. Further, not only the storage medium in which the above program is recorded, but also the program itself is included in each example embodiment. In addition, one or more components included in the above-described example embodiments may be a circuit such as an application specific integrated circuit (ASIC), a field programmable gate array (FPGA) configured to implement the functions of each component.

As the storage medium, for example, a floppy (registered trademark) disk, a hard disk, an optical disk, a magneto-optical disk, a compact disk (CD)-ROM, a magnetic tape, a nonvolatile memory card, or a ROM can be used. Further, the scope of each example embodiment is not limited to the case where the processing is executed by the program alone recorded in the storage medium, and a case where the processing is executed by operating on an operating system (OS) in cooperation with the functions of other software and extension board is also included in the scope of each example embodiment.

The service realized by the functions of the above-described example embodiments may be provided to the user in the form of a software as a service (SaaS).

It should be noted that the above-described example embodiments are merely examples of embodying the present invention, and the technical scope of the present invention should not be limitedly interpreted by these. That is, the present invention can be implemented in various forms without departing from the technical idea or the main features thereof.

The whole or part of the example embodiments disclosed above can be described as, but not limited to, the following supplementary notes.

(Supplementary Note 1)

An information processing device comprising:

an acquisition unit configured to acquire load information based on a load applied to a load measurement device from a sole of a user; and a feature amount extracting unit configured to extract a feature amount indicating a walking environment from time series data in at least one walking cycle included in the load information.

(Supplementary Note 2)

The information processing device according to supplementary note 1, wherein the feature amount extracting unit extracts the feature amount based on a peak included in the time series data.

(Supplementary Note 3)

The information processing device according to supplementary note 2, wherein the feature amount extracting unit extracts the feature amount based on at least one of an appearance time of the peak and size of the peak.

(Supplementary Note 4)

The information processing device according to supplementary note 1, wherein the acquisition unit acquires first time series data measured by a first load measurement device provided on the sole and second time series data measured by a second load measurement device provided between a toe of the sole and the first load measurement device, and wherein the feature amount extracting unit extracts the feature amount based on the first time series data and the second time series data.

(Supplementary Note 5)

The information processing device according to supplementary note 4, wherein the feature amount extracting unit extracts the feature amount based on third time series data acquired by adding the first time series data and the second time series data.

(Supplementary Note 6)

The information processing device according to supplementary note 5, wherein the feature amount extracting unit extracts the feature amount based on a peak included in the third time series data.

(Supplementary Note 7)

The information processing device according to supplementary note 6, wherein the feature amount extracting unit extracts the feature amount based on a plurality of the peaks included in the third time series data.

(Supplementary Note 8)

The information processing device according to any one of supplementary notes 4 to 7, wherein the first load measurement device is provided between a heel and a Lisfranc joint of a foot of the user, and wherein the second load measurement device is provided between a toe and the Lisfranc joint.

(Supplementary Note 9)

The information processing device according to any one of supplementary notes 4 to 8, wherein the feature amount extracting unit extracts the feature amount based on only the first time series data and the second time series data.

(Supplementary Note 10)

The information processing device according to supplementary note 1, wherein the acquisition unit acquires time series data of a load distribution of the sole measured by the load measurement device, and wherein the feature amount extracting unit extracts the feature amount based on the time series data of the load distribution.

(Supplementary Note 11)

The information processing device according to any one of supplementary notes 1 to 10, wherein the feature amount is used to determine whether or not the walking environment of the user is level ground.

(Supplementary Note 12)

The information processing device according to supplementary note 11, wherein the information processing device or the load measurement device is operable in a first mode and a second mode, power consumption thereof in the second mode being smaller than that in the first mode, wherein the information processing device or the load measurement device operates in the first mode in a case where it is determined that the walking environment of the user is level ground, and wherein the information processing device or the load measurement device operates in the second mode in a case where it is determined that the walking environment of the user is not level ground.

(Supplementary Note 13)

A walking environment determination device configured to determine a walking environment of the user based on the feature amount extracted by the information processing device according to any one of supplementary notes 1 to 12.

(Supplementary Note 14)

A walking environment determination system comprising:

the information processing device according to any one of supplementary notes 1 to 12;

a walking environment determination device configured to determine the walking environment of the user; and the load measurement device.

(Supplementary Note 15)

An information processing method comprising:

acquiring load information based on a load applied to a load measurement device from a sole of a user; and extracting a feature amount indicating a walking environment from time series data in at least one walking cycle included in the load information.

(Supplementary Note 16)

A storage medium storing a program that causes a computer to perform:

acquiring load information based on a load applied to a load measurement device from a sole of a user; and extracting a feature amount indicating a walking environment from time series data in at least one walking cycle included in the load information.

REFERENCE SIGNS LIST 1 walking environment determination device
2 information communication terminal
3 server
4 user
5 shoe
6a, 6b load measurement device
7 Lisfranc joint
61 information processing device
101, 201 CPU
102, 202 RAM
103, 203 ROM
104, 204 flash memory
105, 205 communication I/F
106 sensor control device
107 battery
120, 611 acquisition unit
130, 612 feature amount extracting unit 131 walking cycle identification unit
132 feature amount calculation unit
133 time series data processing unit
140 walking environment determination unit
150 storage unit
160 communication unit
170 mode switching unit
206 input device
207 output device

What is claimed is:

1. An information processing device comprising:
a memory configured to store instructions; and
a processor configured to execute the instructions to:
acquire load information based on a load applied to a load sensor from a sole of a user; and
extract a feature amount indicating a walking environment from time series data in at least one walking cycle included in the load information,
wherein the feature amount is used to determine whether or not the walking environment of the user is level ground,
wherein the information processing device or the load sensor is operable in a first mode and a second mode, power consumption thereof in the second mode being smaller than that in the first mode,
wherein the information processing device or the load sensor operates in the first mode in a case where it is determined that the walking environment of the user is level ground, and
wherein the information processing device or the load sensor operates in the second mode in a case where it is determined that the walking environment of the user is not level ground.

2. The information processing device according to claim 1, wherein the feature amount is extracted based on a peak included in the time series data.

3. The information processing device according to claim 2, wherein the feature amount is extracted based on at least one of an appearance time of the peak and size of the peak.

4. The information processing device according to claim 1,
wherein the load sensor includes a first load sensor and a second load sensor,
wherein first time series data measured by the first load sensor provided on the sole and second time series data measured by the second load sensor provided between a toe of the sole and the first load sensor are acquired, and
wherein the feature amount is extracted based on the first time series data and the second time series data.

5. The information processing device according to claim 4, wherein the feature amount is extracted based on third time series data acquired by adding the first time series data and the second time series data.

6. The information processing device according to claim 5, wherein the feature amount is extracted based on a peak included in the third time series data.

7. The information processing device according to claim 6, wherein the feature amount is extracted based on a plurality of the peaks included in the third time series data.

8. The information processing device according to claim 4,
wherein the first load sensor is provided between a heel and a Lisfranc joint of a foot of the user, and
wherein the second load sensor is provided between a toe and the Lisfranc joint.

9. The information processing device according to claim 4, wherein the feature amount is extracted based on only the first time series data and the second time series data.

10. The information processing device according to claim 1,
wherein time series data of a load distribution of the sole measured by the load sensor is acquired, and
wherein the feature amount is extracted based on the time series data of the load distribution.

11. The information processing device according to claim 1,
wherein the processor is further configured to execute the instructions to determine the walking environment of the user based on the feature amount extracted by the information processing device.

12. The information processing device according to claim 1, further comprising the load sensor
wherein the processor is further configured to execute the instructions to determine the walking environment of the user.

13. The information processing device according to claim 1,
further comprising the load sensor,
wherein acquiring the load information comprises acquiring the load information from the load sensor, and
wherein the load sensor is attached to a shoe of the user.

14. An information processing method comprising:
acquiring load information based on a load applied to a load sensor from a sole of a user; and
extracting a feature amount indicating a walking environment from time series data in at least one walking cycle included in the load information,
wherein the feature amount is used to determine whether or not the walking environment of the user is level ground,
wherein the information processing device or the load sensor is operable in a first mode and a second mode, power consumption thereof in the second mode being smaller than that in the first mode,
wherein the information processing device or the load sensor operates in the first mode in a case where it is determined that the walking environment of the user is level ground, and
wherein the information processing device or the load sensor operates in the second mode in a case where it is determined that the walking environment of the user is not level ground.

15. A non-transitory storage medium storing a program that causes a computer to perform:
acquiring load information based on a load applied to a load sensor from a sole of a user; and
extracting a feature amount indicating a walking environment from time series data in at least one walking cycle included in the load information,
wherein the feature amount is used to determine whether or not the walking environment of the user is level ground,
wherein the information processing device or the load sensor is operable in a first mode and a second mode, power consumption thereof in the second mode being smaller than that in the first mode,
wherein the information processing device or the load sensor operates in the first mode in a case where it is determined that the walking environment of the user is level ground, and wherein the information processing device or the load sensor operates in the second mode in a case where it is determined that the walking environment of the user is not level ground.

* * * * *